United States Patent [19]

Kawai et al.

[11] Patent Number: 5,616,613

[45] Date of Patent: Apr. 1, 1997

[54] PLATINUM(II) COMPLEX AND MALIGNANT TUMOR TREATMENT AGENT

[75] Inventors: Hideki Kawai; Masami Tamaoka, both of Kamakura; Yukie Saito, Yokosuka, all of Japan

[73] Assignee: Toray Industries, Inc., Japan

[21] Appl. No.: 557,078

[22] PCT Filed: Apr. 19, 1995

[86] PCT No.: PCT/JP95/00775

§ 371 Date: Jan. 29, 1996

§ 102(e) Date: Jan. 29, 1996

[87] PCT Pub. No.: WO95/28408

PCT Pub. Date: Oct. 26, 1995

[30] Foreign Application Priority Data

Apr. 19, 1994 [JP] Japan .................... 6-080642

[51] Int. Cl.[6] .................... A61K 31/28; C07F 15/00
[52] U.S. Cl. .................... 514/492; 549/210; 549/212; 549/297; 556/137
[58] Field of Search .................... 556/137; 514/492; 549/210, 212, 297

[56] References Cited

FOREIGN PATENT DOCUMENTS

| 57-156416 | 9/1982 | Japan . |
| 60-10952 | 1/1985 | Japan . |
| 1-311089 | 12/1989 | Japan . |
| 2-45494 | 2/1990 | Japan . |
| 5-178873 | 7/1993 | Japan . |

OTHER PUBLICATIONS

"The Pharmaceutical Stabilization of the Clinical Anticancer Drug Dach–Platinum–TMA (NSC271674)" P.J. Andrulis, Jr. et al, Proceedings of the Fifth International Symposium on Platinum and Other Metal Coordination Compounds in Cancer Chemotherapy Abano, Padua, Italy–Jun. 29–Jul. 2, 1987, pp. 450–455.

*Primary Examiner*—Porfirio Nazario-Gonzalez
*Attorney, Agent, or Firm*—Austin R. Miller

[57] ABSTRACT

Novel platinum(II) complexes represented by the general formula

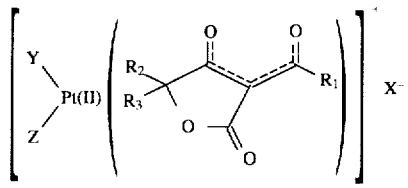

in which $R_1$ represents a lower hydrocarbon radical of 1 to 3 carbon atoms, $R_2$ and $R_3$ each independently represent a hydrogen atom or a lower hydrocarbon radical of 1 to 3 carbon atoms, or $R_2$ and $R_3$ together may form —$(CH_2)_4$— or —$(CH_2)_5$—, Y and Z each independently represent an ammonia molecule or a monodentate amine of 1 to 7 carbon atoms or X and Y together may form a bidentate diamine of 2 to 10 carbon atoms, and $X^-$ represents an inorganic acid anion or an organic carboxylate anion, and agents for treating malignant tumors which contain them as effective components. The compounds are effective against cisplatin-resistant tumors, are soluble enough for intravenous administration, are stable in aqueous solution, and have excellent antitumor activity.

4 Claims, No Drawings

PLATINUM(II) COMPLEX AND MALIGNANT TUMOR TREATMENT AGENT

This application was filed under 35 U.S.C. §371 as a request for U.S. examination of International application No. PCT/JP95/0075 filed on Apr. 10, 1995.

1. Technical Field

The present invention relates to a novel platinum(II) complex and to an agent for treating malignant tumors which contains it as effective component.

2. Background Art

A number of platinum(II) complexes with antitumor activity have been reported, including cis-diamminedichloroplatinum(II) complex (cisplatin) (for example, Japanese Unexamined Patent Publication Nos. 1-311089 and 2-45494).

However, although cisplatin and carboplatin have been known to be very effective against testicular carcinoma and the like, there have been problems of resistance to and thus lowered potency of cisplatin and carboplatin when they are readministered to recurrent patients.

In addition, most of the hitherto known complexes have had disadvantages such as low solubility, either making it impossible to employ intravenous administration which is the method of administration for platinum complexes (for example, cyclobutane-1,1-dicarboxylate, Japanese Unexamined Patent Publication No. 60-10952), or giving them poor stability in aqueous solutions (for example, trimellitic acid, J. P. Andrelius et al., Proceedings of the Fifth International Symposium on Other Metal Compounds in Cancer Chemotherapy, 450 (1987)). The platinum complex described in Japanese Unexamined Patent Publication No. 5-178873 is soluble enough for intravenous administration, but when the hydrophobicity of its substituents increases, the water-solubility of the platinum complex is reduced.

DISCLOSURE OF THE INVENTION

It is an object of the present invention to overcome the above-mentioned disadvantages of the prior art by providing an agent for treating malignant tumors which is based on the discovery of a complex with antitumor activity which has an effect against cisplatin-resistant carcinoma, which is soluble enough for intravenous administration, and which is stable in aqueous solution.

The aforementioned object is achieved by the following invention.

That is, the present invention relates to a novel platinum(II) complex represented by the following general formula (A)

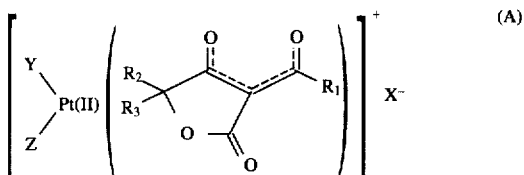

in which $R_1$ represents a lower hydrocarbon radical of 1 to 3 carbon atoms, $R_2$ and $R_3$ each independently represent a hydrogen atom or a lower hydrocarbon radical of 1 to 3 carbon atoms, or $R_2$ and $R_3$ together may form —$(CH_2)_4$— or —$(CH_2)_5$—, Y and Z each independently represent an ammonia molecule or a monodentate amine of 1 to 7 carbon atoms or X and Y together may form a bidentate diamine of 2 to 10 carbon atoms, and $X^-$ represents an inorganic acid anion or an organic carboxylate anion, as well as an agent for treating malignant tumors which contains the compound as an effective component.

BEST MODE FOR CARRYING OUT THE INVENTION

In the compound of formula (A), the lower hydrocarbon radical of 1 to 3 carbon atoms is preferably an alkyl or alkenyl radical, and may specifically be methyl, ethyl, propyl, vinyl, isopropyl, allyl or isopropenyl, with methyl being particularly preferred.

The moiety,

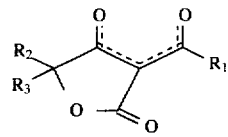

bonded to the platinum in formula (A) exhibits a tautomerism represented by

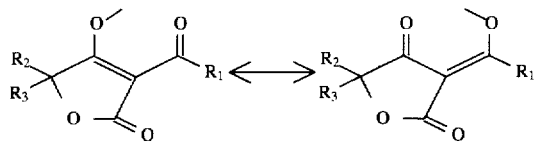

When Y and Z are amines with one nitrogen atom, they are preferably amines having a hydrocarbon radical of 1 to 10 carbon atoms. Specific examples thereof include n-propylamine, iso-propylamine, n-butylamine, n-hexylamine, n-octylamine, cyclopropylamine, cyclobutylamine, cyclopentylamine and cyclohexylamine.

Examples of the bidentate diamine formed by Y and Z together include unsubstituted and substituted 1,2-diaminoethane, unsubstituted and substituted 1,3-diaminopropane, unsubstituted and substituted 1,4-diaminobutane and unsubstituted and substituted 2-aminomethylpyridine. The substituents on these diamines are preferably radicals composed of carbon and hydrogen or of carbon, hydrogen and oxygen, and have 1 to 10 carbon atoms.

Preferred examples of substituted 1,2-diaminoethane include 1-methyl-1,2-diaminoethane, 1-ethyl-1,2-diaminoethane, 1-methyl-1-ethyl-1,2-diaminoethane, 1-phenyl-1,2-diaminoethane, N-methyl-1,2-diaminoethane, N-cyclopentyl-1,2-diaminoethane, N-cyclohexyl-1,2-diaminoethane, 1,2-diaminocyclopentane, 1,2-diaminocyclohexane, 1,2-diaminocycloheptane, 1-(aminomethyl)-cyclopentylamine, 1-(aminomethyl)cyclooctylamine, 3-aminopyrrolidine, 2-(aminomethyl)pyrrolidine, 2-(1-aminoethyl)-pyrrolidine, N-(1-aminoethyl)-morpholine, 2-(aminomethyl)aziridine, 2-(methylamino)-azetidine, bicyclo[2,2,1]heptanediamine.

Preferred examples of substituted 1,3-diaminopropane include 2,2-dimethyl-1,3-diaminopropane, 2,2-diethyl-1,3-diaminopropane, 2-(n-butyl)-1,3-diaminopropane, 2-(n-hexyl)-1,3-diaminopropane, 2-methyl-2-methoxy-1,3-diaminopropane, 2,2-bis(hydroxymethyl)-1,3-diaminopropane, 2,2-bis(methoxyethyl)-1,3-diaminopropane, 1,1-bis(aminomethyl)-cyclopentane, 1,1-bis(aminoethyl)cyclohexane, 4,4-bis(aminomethyl)-tetrahydropyran, 1,3-diaminocyclohexane, 2-(aminomethyl)-cyclopentane, 2-(aminomethyl)-cyclohexane and N-cyclopentyl-1,3-diaminopropane.

Preferred examples of 1,4-diaminobutane include 1-methyl-1,4-diaminobutane, 2-methyl-1,4-diaminobutane, 1-ethyl-1,4-diaminobutane, 1,1-dimethyl-1,4-diaminobutane, 2,2-dimethyl-1,4-diaminobutane, 1,2-dimethyl-1,4-diaminobutane and 1,3-dimethyl-1,4-diaminobutane.

Preferred examples of substituted 2-aminomethylpyridine include 2-(1-aminoethyl)-pyridine, 2-(N-methylaminomethyl)pyridine and 2-(N-ethylaminoethyl)pyridine.

Preferably, Y and Z are ammonia molecules or a molecule formed by Y and Z together and represented by the following formula,

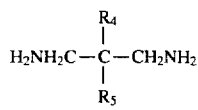

in which $R_4$ and $R_5$ each independently represent a hydrogen atom or a hydrocarbon radical of 1 to 7 carbon atoms, or $R_4$ and $R_5$ together form $—(CH_2)_1—$ (in which 1 is an integer of 3 to 5) or $—(CH_2)_2—O—(CH_2)_2—$.

The present inventors have found that a complex can be synthesized in which one molecule of a deprotonated derivative of a five-membered ring compound (B) with the following structure,

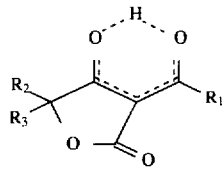

in which compound (B) exhibits the tautomerism represented by

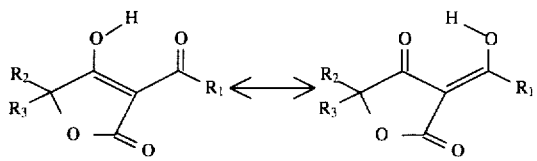

is bonded to platinum(II) whose ligands are Y and Z. These complexes are highly soluble in water, stable in aqueous solution and have strong antitumor effects.

These compounds may be synthesized by processes represented by the following general equations (I) and (II).

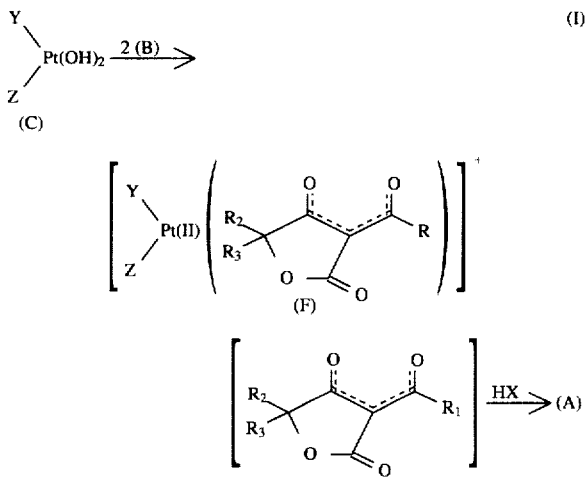

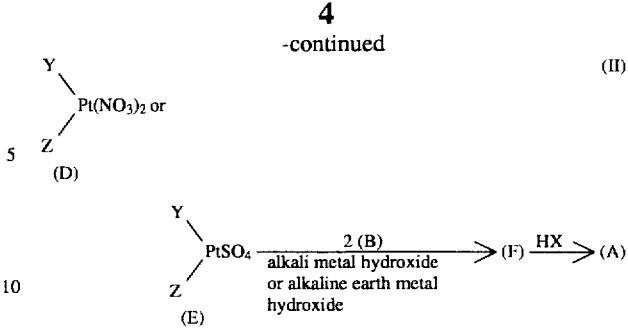

Compound (C) may be obtained by passing compound (D) through a strong ion-exchange resin.

Compounds (D) and (E), which are the materials for synthesizing the platinum complex of the present invention, can be obtained by publicly known methods, for example by treating a compound represented by the following formula (G) with silver nitrate or silver sulfate according to the procedure described in the Journal of Pharmaceutical Sciences, 65, 315, (1976).

wherein Hal represents a halogen.

The alkali metal hydroxide used in reaction (II) is preferably NaOH or KOH. The alkaline earth metal hydroxide used is preferably $Ba(OH)_2$ or $Ca(OH)_2$.

The compound represented by formula (B), another material, may be synthesized by a publicly known method, for example the one described in E. Benary, Berichte 42, 3912 (1909) or the one described D. J. Ager, et al., Tetrahedron Lett., 29, 4807 (1988).

The synthesis intermediate represented by formula (F) may be synthesized according to the method described in Japanese Unexamined Patent Publication No. 5-178873. Compound (B) may be used at a molar ratio of 2 with respect to compounds (C), (D) and (E), or in excess thereof.

Compound (A) of the present invention may be synthesized using 1 molar equivalent of the inorganic acid represented by HX with respect to compound (F). There is also no problem with using an excess of that amount. The compound used as HX may be tetrafluoroboric acid, perchloric acid, hexafluorophosphoric acid or trifluoroacetic acid.

The treatment agent containing an effective amount of the platinum complex of the present invention may be clinically administered orally or parenterally. The agent may be in the form of a tablet, sugar-coated tablet, pill, capsule, powder, lozenge, solution, suppository, injection or the like, and it may be formulated using a pharmaceutically acceptable excipient. Examples of such excipients include lactose, sucrose, glucose, sorbitol, mannitol, potato starch, amylopectin, other various starches, cellulose derivatives (such as carboxymethyl cellulose and hydroxyethyl cellulose), gelatin, magnesium stearate, polyvinyl alcohol, polyethylene glycol wax, gum arabic, talc, titanium dioxide, vegetable oils such as olive oil, peanut oil and sesame oil, paraffin oil, neutral fat base, ethanol, propylene glycol, physiological saline, sterilized water, glycerin, coloring agents, flavoring agents, concentrating agents, stabilizers, isotonic agents, buffering agents and other pharmaceutically acceptable excipients.

The treatment agent of the present invention preferably contains the platinum complex of the present invention in an amount of 0.001–85% by weight, and most preferably 0.005–60% by weight.

Although the dosage of the treatment agent varies mainly depending on the symptoms of a patient, it is generally 0.005–200 mg, and preferably 0.01–50 mg, for an adult per kg of body weight per day.

The invention will now be further illustrated in detail giving examples of production of platinum complexes and water solubilities of the resulting platinum complexes.

EXAMPLE 1

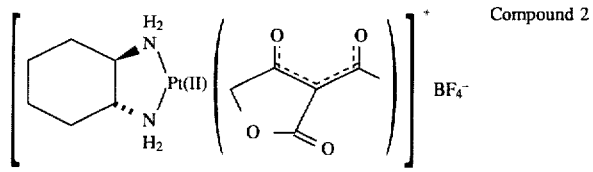

Compound 2

First, 1.36 g (9.5 mmol) of 3-acetyltetrahydrofuran-2,4-dione was dissolved in 15 ml of water and cooled. Then, 67 ml (4.75 mmol) of an aqueous solution of [Pt (trans-1-dach)(OH)$_2$] was added dropwise with a dropping funnel. After 4 hours of stirring, the water was distilled off with a rotary evaporator. After addition of THF and pulverization of the mixture, it was filtered and dried to obtain 2.65 g of a yellow powder. This was dissolved in water and purified by liquid chromatography (developing solvent: H$_2$O:MeOH=1:9) using a column packed with MCI-GEL CHP 20P, to obtain 2.10 g of a crystalline product (compound 1).

The melting point, elementary analysis data and IR and NMR spectrum data of the resulting complex are shown below.

Melting point: 250° C. (decomposed)

Elementary analysis for C$_{18}$H$_{32}$N$_2$O$_{12}$Pt Calculated: C 32.58; H 4.83; N 4.22; Pt 29.41 Found: C 32.56; H 4.82; N 4.26; Pt 29.50

$^1$H-NMR (400 MHz, D$_2$O)δ: 1.21 (2H, brt. J=10 Hz), 1.39 (2H, m), 1.63 (2H, m), 2.11 (2H, brd, J=11 Hz), 2.32 (3H, s), 2.35 (3H, s), 2.58 (2H, m), 4.41 (2H, s), 4.51 (2H, s).

IR (KBr disc) cm$^{-1}$: 3390, 3162, 3076, 1752, 1649, 54 1605, 1497, 1460, 1056, 1025, 768, 702, 605. Solubility (in water): 30–40 mg/ml A 1.83 g (3 mmol) portion of the crystals of the resulting compound 1 was dissolved in 30 ml of methanol. To this was added 700 mg of tetrafluoroboric acid in water (42%), and the mixture was stirred at room temperature for 10 minutes. The solvent was concentrated with a rotary evaporator under reduced pressure, 50 ml of ethyl acetate was added, and the mixture was stirred for hours. The colorless crystals were filtered out and then washed with ethyl acetate. The resultant crude product was recrystallized with methanol/ethyl acetate to obtain 1.34 g of a colorless crystalline product (compound 2).

Melting point: 238.1° C. (decomposed)

Elementary analysis for C$_{12}$H$_{19}$BF$_4$N$_2$O$_4$Pt Calculated: C 26.83; H 3.57; N 5.21; Pt 36.32 Found: C 26.88; H 3.64; N 5.25; Pt 36.49

$^1$H-NMR (500 MHz, D$_2$O)δ: 1.04 (2H, m), 1.22 (2H, m), 1.46 (2H, brd, J=4.77 Hz), 1.95 (2H, bed, J=11.72 Hz), 2.18 (3H, s), 2.42 (2H, brd, J=8.79 Hz), 4.37 (2H, s).

IR (KBr disc) cm$^{-1}$: 3052, 2950, 1738, 1607, 1493, 1342, 1265, 1180, 1031, 766, 704, 658.

EXAMPLE 2

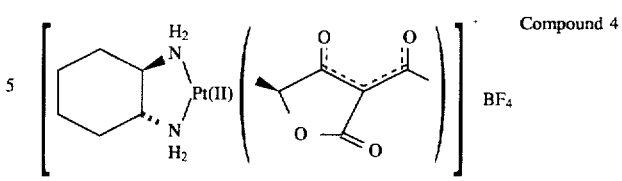

Compound 4

First, 3.90 g (24.5 mmol) of 3-acetyl-(5S)methyltetrahydrofuran-2,4-dione was dissolved in 100 ml of water and cooled. Then, 170 ml (12.25 mmol) of an aqueous solution of [Pt(trans-1-dach)(OH)$_2$]9 was added dropwise with a dropping funnel. After 4 hours of stirring, the water was distilled off with a rotary evaporator. After addition of THF and pulverization of the mixture, it was filtered and dried to obtain 8.30 g of a yellow powder. This was dissolved in water and purified by liquid chromatography (developing solvent: H$_2$O: MeOH=1:9) using a column packed with MCI-GEL CHP P, to obtain 7.95 g of a crystalline product (compound 3).

The melting point, elementary analysis data and IR and NMR spectrum data of the resulting complex are shown below.

Melting point: 250°–254° C. (decomposed)

Elementary analysis for C$_{20}$H$_{36}$N$_2$O$_{12}$Pt Calculated: C 34.74; H 5.25; N 4.05; Pt 28.21 Found: C 34.75; H 5.20; N 4.05; Pt 28.22

$^1$H-NMR (500 MHz, D$_2$O)δ: 1.25 (2H, brt. J=8 Hz), 1.42 (3H, d, J=7 Hz), 1.43 (2H, m), 1.49 (3H, d, J=7 Hz), 1.67 (2H, m), 2.15 (2H, brd, J=12 Hz), 2.37 (3H, s), 2.39 (3H, s), 2.62 (2H, m), 4.58 (1H, q, J=7 Hz), 4.79 (1H, q, J=7 Hz).

IR (KBr disc) cm$^{-1}$: 3346, 3170, 3082, 2938, 1750, 1651, 1603, 1562, 1543, 1493, 1460, 540, 437, 416.

Solubility (in water): 30–40 mg/ml

A 6.19 g (8 mmol) portion of the crystals of the resulting compound 3 was dissolved in 120 ml of methanol. To this was added 2.2 g of tetrafluoroboric acid in water (42%), and the mixture was stirred at room temperature for 20 minutes. The solvent was concentrated with a rotary evaporator under reduced pressure, 100 ml of ethyl acetate was added, and the mixture was stirred for 2 hours.

The colorless crystals were filtered out and then washed with ethyl acetate. The resultant crude product was recrystallized with methanol/ethyl acetate to obtain 4.79 g of a colorless crystalline product (compound 4).

Melting point: 228.0° C. (decomposed)

Elementary analysis for C$_{13}$H$_{21}$BF$_4$N$_2$O$_4$Pt Calculated: C 28.33; H 3.84; N 5.08; Pt 35.39 Found: C 28.39; H 3.85; N 5.03; Pt 36.32

$^1$H-NMR (500 MHz, D$_2$O)δ: 1.24 (2H, bt, J=9.75 Hz), 1.42 (2H, m), 1.49 (3H, d, J=6.70 Hz), 1.67 (2H, m), 2.15 (2H, bd, J=12.2 Hz), 2.38 (3H, s), 2.61 (2H, m), 4.80 (1H, q, J=6.70 Hz).

IR (KBr disc) cm$^{-1}$: 3034, 2942, 1758, 1736, 1605, 1499, 1259, 1067, 1029, 781.

EXAMPLE 3

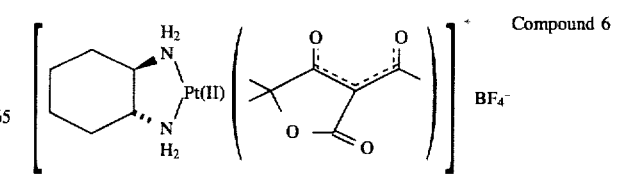

Compound 6

First, 1.76 g (10 mmol) of 3-acetyl-5,5-dimethyltetrahydrofuran-2,4-dione was dissolved in 20 ml of water and cooled. Then, 70 ml (5.0 mmol) of an aqueous solution of [Pt (trans-1-dach)(OH)$_2$] was added dropwise with a dropping funnel. After 4 hours of stirring, the water was distilled off with a rotary evaporator. After addition of THF and pulverization of the mixture, it was filtered and dried to obtain 3.12 g of a yellow powder. This was dissolved in water and purified by liquid chromatography (developing solvent: H$_2$O:MeOH=1:9) using a column packed with MCI-GEL CHP 20P to obtain 2.80 g of a crystalline product (compound 5).

The melting point, elementary analysis data and IR and NMR spectrum data of the resulting complex are shown below.

Melting point: 220° C. (decomposed)

Elementary analysis for C$_{22}$H$_{36}$N$_2$O$_{10}$Pt Calculated: C 38.65; H 5.27; N 4.09; Pt 28.55 Found: C 38.72; H 5.28; N 4.09; Pt 28.60

$^1$H-NMR (400 MHz, D$_2$O)δ: 1.21 (2H, brt. J=10 Hz), 1.38 (3H, s), 1.40 (2H, m), 1.45 (3H, s), 1.46 (3H, s), 1.62 (2H, m), 2.11 (2H, brd, J=12 Hz), 2.34 (3H, s), 2.35 (3H, s), 2.58 (2H, m).

IR (KBr) cm$^{-1}$: 3428, 3076, 2936, 1738, 1709, 1638, 1607, 1522, 1491, 1464, 1369, 1311, 1294, 1265, 1232, 1170, 1149, 1033, 977, 961, 658, 613, 586, 532.

Solubility (in water): 10–20 mg/ml

A 2.59 g (4 mmol) portion of the crystals of the resulting compound 5 was dissolved in 30 ml of methanol. To this was added 920 mg of tetrafluoroboric acid in water (42%), and the mixture was stirred at room temperature for 15 minutes. The solvent was concentrated with a rotary evaporator under reduced pressure, 50 ml of ethyl acetate was added, and the mixture was stirred for hours. The colorless crystals were filtered out and then washed with ethyl acetate. The resultant crude product was recrystallized with methanol/ethyl acetate to obtain 1.90 g of a colorless crystalline product (compound 6).

The melting point, elementary analysis data and IR and NMR spectrum data of the resulting complex are shown below.

Melting point: 236.0° C. (decomposed)

Elementary analysis for C$_{14}$H$_{23}$BF$_4$N$_2$O$_4$Pt Calculated: C 29.75; H 4.10; N 4.96; Pt 34.51 Found: C 29.90; H 4.20; N 4.85; Pt 34.54

$^1$H-NMR (500 MHz, D$_2$O)δ: 1.38 (2H, bt, J=9.75 Hz), 1.56 (2H, m), 1.63 (3H, s), 1.64 (3H, s), 2.29 (2H, bt, J=14.05 Hz), 2.52(3H, s), 2.76 (2H, m).

IR (KBr disc) cm$^{-1}$: 3034, 1769, 1611, 1493, 1315, 1255, 1176, 1029.

EXAMPLE 4

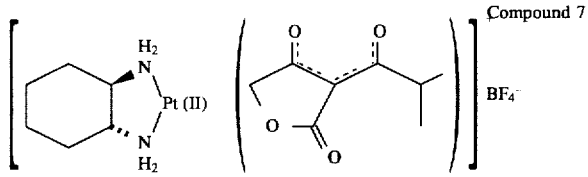

Compound 7

First, 880 mg (2.0 mmol) of 3-isobutyryltetrahydrofuran-2,4-dione was dissolved in 5 ml of water and cooled. Then, 12 ml (1.0 mmol) of an aqueous solution of [Pt (trans-1-dach)(OH)$_2$] was added dropwise with a dropping funnel. After 4 hours of stirring, the water was distilled off with a rotary evaporator. After addition of THF and pulverization of the mixture, it was filtered and dried to obtain 620 mg of a yellow powder. This was dissolved in water and purified by liquid chromatography (developing solvent: H$_2$O: MeOH= 1:9) using a column packed with MCI-GEL CHP 20P, to obtain 562 mg of a crystalline product.

A 390 mg (0.630 mmol) portion of the obtained crystals was dissolved in 8 ml of methanol. To this was added 139 mg of tetrafluoroboric acid in water (42%), and the mixture was stirred at room temperature for 20 minutes. The solvent was concentrated with a rotary evaporator under reduced pressure, 10 ml of ethyl acetate was added, and the mixture was stirred for 2 hours.

The colorless crystals were filtered out and then washed with ethyl acetate. The resultant crude product was recrystallized with methanol/ethyl acetate to obtain 291 mg (83.9%) of a colorless crystalline product (compound 7).

The melting point, elementary analysis data and IR and NMR spectrum data of the resulting complex are shown below.

Melting point: 248.0° C. (decomposed)

Elementary analysis for C$_{14}$H$_{23}$BF$_4$N$_2$O$_4$Pt Calculated: C 29.75; H 4.10; N 4.96; Pt 34.51 Found: C 29.82; H 4.08; N 4.88; Pt 34.81

$^1$H-NMR (400 MHz, D$_2$O)δ: 1.07 (3H, d, J=6.59 Hz), 1.08 (3H, d, J=6.59 Hz), 1.19 (2H, m), 1.39 (2H, m), 1.61 (2H, m), 2.09 (2H, m), 2.56 (2H, m), 3.66 (1H, septet, J=6.59 Hz), 4.49 (2H, s).

IR (KBr disc) cm$^{-1}$: 3040, 1771, 1605, 1493, 1340, 1245, 1181, 1060, 1031, 783.

EXAMPLE 5

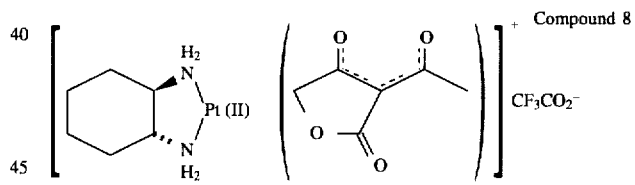

Compound 8

A 3.05 g (5.16 mmol) portion of compound 1 was dissolved in 30 ml of methanol. To this was added 0.46 ml of trifluoroacetic acid, and the mixture was stirred at room temperature for 30 minutes. The solvent was concentrated with a rotary evaporator under reduced pressure, 50 ml of ethyl acetate was added, and the mixture was stirred for 2 hours. The colorless crystals were filtered out and then washed with ethyl acetate. The resultant crude product was recrystallized with methanol/ethyl acetate to obtain 2.58 g (88%) of a colorless crystalline product (compound 8).

The melting point, and IR and NMR spectrum data of the resulting complex are shown below.

Melting point: 244.9° C. (decomposed)

$^1$H-NMR (400 MHz, D$_2$O)δ: 4.39 (2H, s), 2.56 (2H, m), 2.33 (3H, s), 2.1 (2H, m), 1.62 (2H, m), 1.37 (2H, m), 1.17 (2H, m).

IR (KBr disc) cm$^{-1}$: 2932, 1727, 1560, 1493, 1448, 1363, 1270, 1178; 1054, 934, 768, 665.

Solubility (in water): 50 mg/ml +

EXAMPLE 6

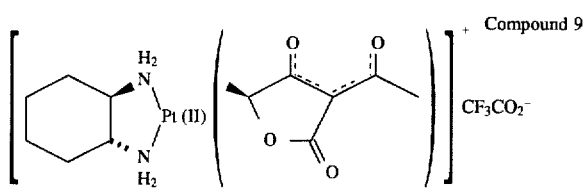
Compound 9

A 6.19 g (9.99 mmol) portion of compound 3 was dissolved in 30 ml of methanol. To this was added 0.92 ml of trifluoroacetic acid, and the mixture was stirred at room temperature for 30 minutes. The solvent was concentrated with a rotary evaporator under reduced pressure, 50 ml of ethyl acetate was added, and the mixture was stirred for 2 hours. The colorless crystals were filtered out and then washed with ethyl acetate. The resultant crude product was recrystallized with methanol/ethyl acetate to obtain 5.02 g (87%) of a colorless crystalline product (compound 9).

The melting point, and IR and NMR spectrum data of the resulting complex! are shown below.

Melting point: 236.8° C. (decomposed)

$^1$H-NMR (400 MHz, $D_2O$)δ: 4.75 (1H, q, J=6.83 Hz), 2.56 (2H, m), 2.32 (3H, s), 2.11 (2H, m), 1.61 (2H, m), 1.44 (3H, d, J=6.83 Hz), 1.37 (2H, m), 1.19 (2H, m).

IR (KBr disc) $cm^{-1}$: 3826, 3716, 2940, 1746, 1688, 1605, 1491, 1205, 1176, 1133, 1094, 1069, 1038, 832, 799, 719, 702, 636.

Solubility (in water): 50 mg/ml +

EXAMPLE 7

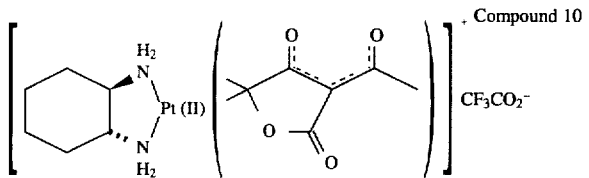
Compound 10

A 970 mg (1.50 mmol) portion of compound 5 was dissolved in 10 ml of methanol. To this was added 0.14 ml of trifluoroacetic acid, and the mixture was stirred at room temperature for 30 minutes. The solvent was concentrated with a rotary evaporator under reduced pressure, 50 ml of ethyl acetate was added, and the mixture was stirred for 2 hours. The colorless crystals were filtered out and then washed with ethyl acetate. The resultant crude product was recrystallized with methanol/ethyl acetate to obtain 793 mg (89%) of a colorless crystalline product (compound 10).

The melting point, and IR and NMR spectrum data of the resulting complex are shown below.

Melting point: 243.6° C. (decomposed)

$^1$H-NMR (D20, 400 MHz, ppm): 2.56 (m, 2H), 2.33 (s, 3H), 2.09 (bt, 2H, J=13.67), 1.61 (m, 2H), 1.45 (s, 3H), 1.44 (s, 3H), 1.38 (m, 2H), 1.19 (m, 2H).

IR (KBr disc) $cm^{-1}$: 3010, 2930, 1744, 1688, 1605, 1491, 1423, 1369, 1313, 1257, 1201, 1174, 1135, 1027, 977, 936, 839, 791, 719, 692, 644, 609.

Solubility (in water): 50 mg/ml +

EXAMPLE 8

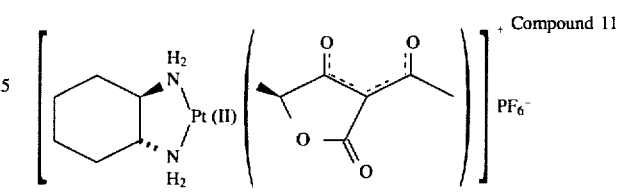
Compound 11

A 6.19 g (9.99 mmol) portion of compound 3 was dissolved in 30 ml of methanol. To this was added 2.43 g of hexafluorophosphoric acid, and the mixture was stirred at room temperature for 30 minutes. The solvent was concentrated with a rotary evaporator under reduced pressure, 50 ml of ethyl acetate was added, and the mixture was stirred for 2 hours. The colorless crystals were filtered out and then washed with ethyl acetate. The resultant crude product was recrystallized with methanol/ethyl acetate to obtain 4.81 g (79%) of a colorless crystalline product (compound 11).

The melting point, and IR and NMR spectrum data of the resulting complex are shown below.

Melting point: 262.8° C. (decomposed)

$^1$H-NMR (400 MHz, DMF-d7)δ: 6.90 (2H, brd, J=7.83, 21.4Hz), 6.20 (2H, m), 4.76 (1H, q, J=6.83 Hz), 2.76 (2H, m), 2.32 (3H, s), 2.13 (2H, bd, J=11.7 Hz), 1.58 (4H, m), 1.40 (3H, d, J=6.83 Hz), 1.22 (2H, m).

IR (KBr disc) $cm^{-1}$: 3288, 3018, 1758, 1738, 1613, 1493, 1176, 1093, 1067, 1009, 849, 561.

EXAMPLE 9

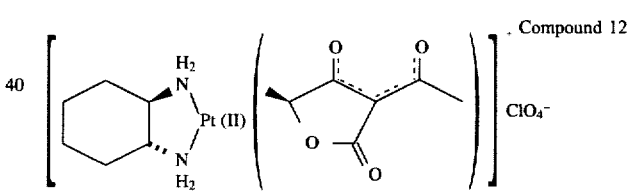
Compound 12

A 3.10 g (5.00 mmol) portion of compound 3 was dissolved in 30 ml of methanol. To this was added 860 mg of perchloric acid, and the mixture was stirred at room temperature for 30 minutes. The solvent was concentrated with a rotary evaporator under reduced pressure, 50 ml of ethyl acetate was added, and the mixture was stirred for hours. The colorless crystals were filtered out and then washed with ethyl acetate. The resultant crude product was recrystalized with methanol/ethyl acetate to obtain 2.37 g (84%) of a colorless crystalline product (compound 12).

The IR and NMR spectrum data of the resulting complex are shown below.

$^1$H-NMR (400 MHz, DMF-d7)δ:6.91 (2H, bdd, J=7.35, 42Hz), 6.22 (2H, m), 4.76 (1H, q, J=6.83 Hz), 2.79 (2H, m), 2.32 (3H, s), 2.13 (2H, bd, J=11.7), 1.59 (4H, m), 1.39 (3H, d, J=6.83 Hz), 1.22 (2H, m).

IR (KBr disc) $cm^{-1}$: 3034, 2942, 2868, 1734, 1613, 1497, 1456, 1402, 1371, 1336, 1261, 1234, 1214, 1178, 1071, 1027, 779, 706, 630.

EXAMPLE 10

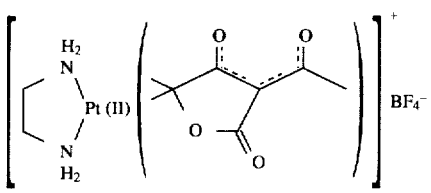

Compound 14

First, 3.40 g (20 mmol) of 3-acetyl-5,5-dimethyltetrahydrofuran-2,4-dione was dissolved in 40 ml of water and cooled. Then, 100 ml (10.0 mmol) of an aqueous solution of [Pt (1,2-diaminoethane)(OH)$_2$] was added dropwise with a dropping funnel. After 8 hours of stirring, the water was distilled off with a rotary evaporator. After adding methanol and filtering off the insoluble portion, the filtrate was concentrated. The resultant crude product was dissolved in water and purified by liquid chromatography (developing solvent: H$_2$O) using a column packed with MCI-GEL CHP 20P, to obtain 4.98 g of a crystalline product (compound 13: solubility (in water)=10–20 mg/ml).

A 4.98 g (8.39 mmol) portion of the obtained crystals was dissolved in 15 ml of methanol. To this was added 1.75 ml of tetrafluoroboric acid in water (42%), and the mixture was stirred at room temperature for 15 minutes. The solvent was concentrated with a rotary evaporator under reduced pressure, 50 ml of ethyl acetate was added, and the mixture was stirred for 2 hours. The colorless crystals were filtered out and then washed with ethyl acetate. The resultant crude product was dissolved in water and purified by liquid chromatography (developing solvent: H$_2$O) using a column packed with MCI-GEL CHP 20P, to obtain 3.65 g of a crystalline product (compound 14: solubility (in water)=20 mg/ml +).

The melting point, elementary analysis data and IR and NMR spectrum data of the resulting complex are shown below.

Melting point: 218.3° C. (decomposed)

Elementary analysis for C$_{10}$H$_{17}$BF$_4$N$_2$O$_4$Pt Calculated: C 23.50; H 3.35; N 5.48; Pt 38.17 Found: C 29.59; H 3.34; N 5.50; Pt 38.50

$^1$H-NMR (400 MHz, CD$_3$OD)δ: 1.43 (6H, s), 2.35 (3H, s), 2.61 (4H, m).

IR (KBr)cm$^{-1}$: 3068, 1738, 1607, 1497, 1311, 1036.

EXAMPLE 11

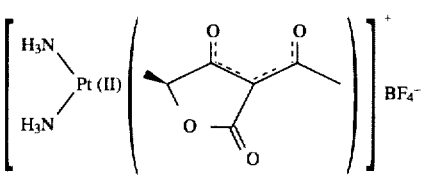

Compound 15

First, 3.12 g (20 mmol) of 3-acetyl-5-methyltetrahydrofuran-2,4-dione was dissolved in 40 ml of water and cooled. Then, 50 ml (10.0 mmol) of an aqueous solution of [(NH$_3$)Pt(OH)$_2$] was added dropwise with a dropping funnel. After 8 hours of stirring, the water was distilled off with a rotary evaporator. After adding methanol and filtering off the insoluble portion, the filtrate was concentrated. The resultant crude product was dissolved in water and purified by liquid chromatography (developing solvent: H$_2$O) using a column packed with MCI-GEL CHP 20P, to obtain 4.26 g of a crystalline product (compound 16).

The 4.26 g (7.90 mmol) of obtained crystals was dissolved in 15 ml of methanol. To this was added 1.65 ml of tetrafluoroboric acid in water (42%), and the mixture was stirred at room temperature for 30 minutes. The solvent was concentrated with a rotary evaporator under reduced pressure, 50 ml of ethyl acetate was added, and the mixture was stirred for 2 hours. The colorless crystals were filtered out and then washed with ethyl acetate. The resultant crude product was dissolved in water and purified by liquid chromatography (developing solvent: H$_2$O) using a column packed with MCI-GEL CHP 20P, to obtain 3.42 g of a crystalline product (compound 15: solubility (in water)=20 mg/ml +).

The melting point, elementary analysis data and IR and NMR spectrum data of the resulting complex are shown below.

Melting point: 231.9° C. (decomposed)

Elementary analysis for C$_7$H$_{13}$BF$_4$N$_2$O$_4$Pt Calculated: C 17.85; H 2.78; N 5.95; Pt 41.41 Found: C 17.83; H 2.74; N 6.00; Pt 41.77

$^1$H-NMR (400 MHz, D$_2$O)δ: 1.65 (3H, d, J=6.83Hz), 4,80 (1H, q, J=6.83 Hz).

IR (KBr) cm$^{-1}$: 3308, 1752, 1605, 1502, 1334, 1038, 903, 839, 785.

EXAMPLE 13

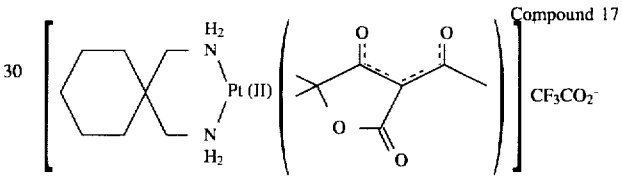

Compound 17

First, 3.40 g (20 mmol) of 3-acetyl-5,5-dimethyltetrahydrofuran-2,4-dione was dissolved in 40 ml of water and cooled. ! Then, 100 ml (10.0 mmol) of an aqueous solution of [Pt(1,1-bis(aminomethyl)cyclohexane(OH)$_2$] was added dropwise with a dropping funnel. After 8 hours of stirring, the water was distilled off with a rotary evaporator. After adding methanol and filtering off the insoluble portion, the filtrate was concentrated. The resultant crude product was dissolved in water and purified by liquid chromatography (developing solvent: H$_2$O: MeOH=7:3) using a column packed with MCI-GEL CHP 20P, to obtain 3.76 g of a crystalline product (compound 18: solubility (in water)=2 mg/ml).

The 3.76 g (5.57 mmol) of obtained crystals was dissolved in 15 ml of methanol. To this was added 1.16 ml of tetrafluoroboric acid in water (42%), and the mixture was stirred at room temperature for 30 minutes. The solvent was concentrated with a rotary evaporator under reduced pressure, 30 ml of ethyl acetate was added, and the mixture was stirred for 1 hour. The colorless crystals were filtered out and then washed with ethyl acetate. The resultant crude product was dissolved in water and purified by liquid chromatography (developing solvent: H$_2$O: MeOH=7:3) using a column packed with MCI-GEL CHP 20P, to obtain 2.93 g of a crystalline product (compound 17: solubility (in water)=20 mg/ml +).

The melting point, elementary analysis data and NMR spectrum data of the resulting complex are shown below.

Melting point: 258.2° C. (decomposed)

Elementary analysis for C$_{18}$H$_{27}$F$_3$N$_2$O$_6$Pt Calculated: C 34.90; H 4.39; N 4.52; Pt 31.49 Found: C 34.97; H 4.28; N 4.36; Pt 31.82

$^1$H-NMR (400 MHz, CD$_3$OD)δ: 1.40 (10H, m), 1.45 (6H, s), 2.38 (3H, s), 2.48 (4H, brs).

EXAMPLE 14

This example illustrates the antitumor activity of compounds of the present invention.

A portion of 1×10$^5$ mouse leukemia L1210 cells subcultured in DBA/2 mice were transplanted in the abdominal cavities of CDF$_1$ mice (male, 6 weeks old, 6–10 animals/group). Each of the test compounds was intraperitoneally administered to the mice on the 1st, th and 9th days after the day of transplantation. Each of the preparations was used after being dissolved in distilled water.

The antitumor activity of the platinum complexes against the L1210 cell-planted mice was evaluated based on the T/C value determined by the following equation.

$$T/C(\%) = \frac{\text{(average survival days of treated mice)}}{\text{(average survival days of control mice)}} \times 100$$

The results are shown in Table 1.

TABLE 1

| Compound | Dose (mg/kg) | T/C (%) | Compound | Dose (mg/kg) | T/C (%) |
|---|---|---|---|---|---|
| 2 | 6.25 | 138 | 11 | 6.25 | 129 |
|   | 12.5 | 168 |    | 12.5 | 138 |
|   | 25   | 146 |    | 25   | 165 |
|   | 50   | 81  |    | 50   | 178 |
|   | 100  | 62  |    | 100  | 170 |
| 4 | 6.25 | 123 | 3  | 18   | 141 |
|   | 12.5 | 141 |    | 27   | 141 |
|   | 25   | 183 |    | 40   | 160 |
|   | 50   | 217 |    | 60   | 185 |
|   | 100  | 150 |    | 90   | 170 |
| 6 | 12.5 | 133 | Cisplatin | 0.25 | 101 |
|   | 25   | 128 |    | 0.5  | 101 |
|   | 50   | 153 |    | 1    | 106 |
|   | 100  | 163 |    | 2    | 123 |
|   | 200  | 210 |    | 4    | 160 |

EXAMPLE 15

A test of the in vitro cytotoxic effect of compound 15 and cisplatin on cisplatin-resistant mouse leukemia L1210 cells was conducted in the following manner.

1×10$^5$ cisplatin-resistant L1210 cells were seeded in a 96-well plate at 100 μl per well. About 100 μl of the drugs at graded dilutions was added to each well. Culturing was then performed at 37° C. for 5 days, and the cells were counted by the XTT colorimetric method. The 50% cell growth inhibition concentration (IC$_{50}$) was calculated to determine the drug's effect.

The results are shown in Table 2

TABLE 2

| Sample | IC$_{50}$ (nM) |
|---|---|
| Compound 15 | 5.26 |
| Cisplatin | 10.66 |

We claim:

1. A novel platinum(II) complex represented by the following general formula (A)

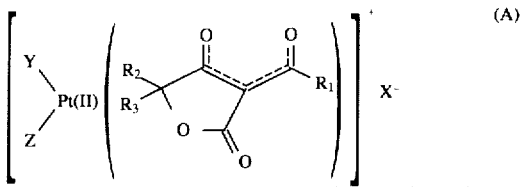

in which R$_1$ represents a lower hydrocarbon radical of 1 to 3 carbon atoms, R$_2$ and R$_3$ each independently represent a hydrogen atom or a lower hydrocarbon radical of 1 to 3 carbon atoms, or R$_2$ and R$_3$ together may form —(CH$_2$)$_4$— or —(CH$_2$)$_5$—, Y and Z each independently represent an ammonia molecule or a monodentate amine of 1 to 7 carbon atoms or X and Y together may form a bidentate diamine of 2 to 10 carbon atoms, and X$^-$ represents an inorganic acid anion or an organic carboxylate anion.

2. A novel platinum(II) complex as claimed in claim 1, wherein the inorganic acid anion is BF$_4^-$, PF$_6^-$ or ClO$_4^-$.

3. A novel platinum(II) complex as claimed in claim 1, wherein the organic acid anion is CF$_3$CO$_2^-$.

4. An agent for treating malignant tumors, whose effective component is a novel platinum(II) complex according to any of claims 1 to 3.

* * * * *

UNITED STATES PATENT AND TRADEMARK OFFICE
CERTIFICATE OF CORRECTION

PATENT NO. : 5,616,613
DATED : April 1, 1997
INVENTOR(S) : Hideki Kawai, Masami Tamaoka and Yukie Saito It is certified that error appears in the above-indentified patent and that said Letters Patent is hereby corrected as shown below:

In Column 1, line 6, please change "PCT/JP95/0075" to --PCT/JP95/00775--.

In Column 5, line 43, please delete "54".

In Column 6, line 12, please change "[Pt (trans-1-dach)(OH)$_2$9" to --[Pt (trans-1-dach)(OH)$_2$]--; and
line 19, please change "MCI-GEL CHP P," to --MCI-GEL CHP 20P,--.

UNITED STATES PATENT AND TRADEMARK OFFICE
CERTIFICATE OF CORRECTION

PATENT NO. : 5,616,613
DATED : April 1, 1997
INVENTOR(S) : Hideki Kawai, Masami Tamaoka and Yukie Saito It is certified that error appears in the above-indentified patent and that said Letters Patent is hereby corrected as shown below:

In Column 8, line 62, please change "2.1 (2H, m)," to --2.11 (2H, m),--.

In Column 10, line 53, please change "hours." to --2 hours.--; and
line 60, please change "(400 MHz, DMF-d7)8: 6.91" to --(400 MHz, DMF-d7)δ: 6.91--.

Signed and Sealed this

Fifth Day of August, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,616,613
DATED      : April 1, 1997
INVENTOR(S) : Hideki Kawai, Masami Tamaoka and Yukie Saito It is certified that error appears in the above-indentified patent and that said Letters Patent is hereby corrected as shown below:

In Column 3, lines 60-65, please change

"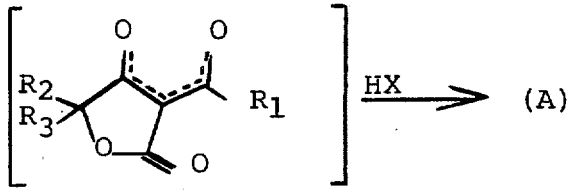"

to

--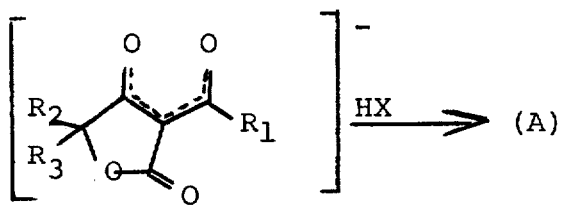--.

Signed and Sealed this

Fourteenth Day of October, 1997

Attest:

BRUCE LEHMAN

Attesting Officer

Commissioner of Patents and Trademarks